US009266104B2

(12) United States Patent
Link

(10) Patent No.: US 9,266,104 B2
(45) Date of Patent: Feb. 23, 2016

(54) THERMOCYCLING DEVICE FOR NUCLEIC ACID AMPLIFICATION AND METHODS OF USE

(75) Inventor: Darren Roy Link, Lexington, MA (US)

(73) Assignee: Raindance Technologies, Inc., Billerica, MA (US)

( * ) Notice: Subject to any disclaimer, the term of this patent is extended or adjusted under 35 U.S.C. 154(b) by 6 days.

(21) Appl. No.: 13/371,217

(22) Filed: Feb. 10, 2012

(65) Prior Publication Data

US 2012/0208241 A1 Aug. 16, 2012

Related U.S. Application Data

(60) Provisional application No. 61/441,992, filed on Feb. 11, 2011.

(51) Int. Cl.

| | |
|---|---|
| ***C12Q 1/68*** | (2006.01) |
| ***C12P 19/34*** | (2006.01) |
| ***B01L 3/02*** | (2006.01) |
| ***B01L 7/00*** | (2006.01) |

(52) U.S. Cl.

CPC ................. *B01L 3/0265* (2013.01); *B01L 7/52* (2013.01); *B01L 2200/0673* (2013.01); *B01L 2300/1827* (2013.01)

(58) Field of Classification Search

CPC ... B01L 3/502; B01L 3/5027; B01L 3/50273; B01L 3/502738; B01L 7/00; B01L 7/52; B01L 2200/0673

See application file for complete search history.

(56) References Cited

U.S. PATENT DOCUMENTS

| | | | | |
|---|---|---|---|---|
| 5,656,493 | A * | 8/1997 | Mullis et al. | 435/286.1 |
| 2009/0226972 | A1 * | 9/2009 | Beer et al. | 435/91.2 |

FOREIGN PATENT DOCUMENTS

| | | | |
|---|---|---|---|
| WO | WO 2005023427 | A1 * | 3/2005 |
| WO | WO 2009015296 | A1 * | 1/2009 |

OTHER PUBLICATIONS

Mahjoob et al. Rapid microfluidic thermal cycler for polymerase chain reaction nucleic acid amplification. Int J Heat Mass Transfer 2008;51:2109-22.*

* cited by examiner

*Primary Examiner* — Young J Kim

(74) *Attorney, Agent, or Firm* — Brown Rudnick LLP; Thomas C. Meyers

(57) ABSTRACT

The present invention provides thermocycling devices useful for amplification of nucleic acids in droplets. The thermocycling device utilizes the flow of one or more fluids through a main compartment at temperatures sufficient to conduct a polymerase chain reaction. Methods of amplifying nucleic acids in droplets are also provided.

21 Claims, 5 Drawing Sheets

TOP

SIDE

TOP

SIDE

THERMOCYCLING DEVICE FOR NUCLEIC ACID AMPLIFICATION AND METHODS OF USE

RELATED APPLICATION

The present application claims the benefit of and priority to U.S. provisional patent application Ser. No. 61/441,992, filed Feb. 11, 2011, the content of which is incorporated by reference herein in its entirety.

FIELD OF THE INVENTION

The present invention generally relates to thermocycling devices and methods for nucleic acid amplification. In particular, the present invention relates to fluid based thermocycling devices and methods for micro PCR.

BACKGROUND OF THE INVENTION

Since the invention of PCR, numerous designs for thermocycling devices have been developed in an effort to increase the throughput, speed sensitivity and specificity of nucleic acid amplification. The trend over the past several years has focused on the development of miniaturized PCR apparatus and tests. Current designs for PCR microchips range from wide chambers of varying sizes and depths to narrow channels (linear or serpentine) and can have a single reaction chamber or arrays of chambers for multiple simultaneous reactions. See e.g., Krick and Wilding, Anal Bioanal Chem, 377:820-825 (2003). Some devices utilize a design format in which the reaction mixture is kept stationary and the temperature of the surrounding reaction chamber is cycled between the different temperatures, while other devices utilize a design format in which the reaction mixture is moved between different fixed temperature zones (e.g., a serpentine channel design; Krick and Wilding). These currently available thermocyclers utilize external electric thermal plates, infrared radiation, or heaters fabricated directly onto the surface of the devices (e.g., tungsten or platinum film) for directly heating and cooling of the PCR reaction mixture (Krick and Wilding).

SUMMARY OF THE INVENTION

The present invention provides thermocycling devices and methods for amplifying nucleic acids which do not rely on the use external electric heating blocks or embedded heaters. More specifically, the present invention provides a fluid-based thermocycling devices and methods for amplifying nucleic acids using the same. The devices and methods of the invention are especially useful for micro PCR, in particular for conducting PCR in droplets. In contrast to previous PCR microchips which utilize linear or serpentine reaction microchannels which cross different temperature zones on an electric thermal substrate, the thermocycling device of the invention utilizes at least one reaction chamber and one or more fluids having different temperatures sufficient for conducting a PCR reaction that contact the reaction chamber in a manner that causes alternating temperatures within the reaction chamber.

The reaction chamber provides housing for one or more droplets, each of which contain a template molecule and reagent sufficient for conducting a PCR reaction (e.g., at least one primer, dNTPs and a polymerase and/or reverse transcriptase). One or more fluid sources contact the chamber to cause alternating temperatures sufficient to conduct a PCR reaction within the chamber. In a particular embodiment, three different fluid sources containing a liquid at a temperature of about 94°-100° C., 50°-65° C. and 68°-72° C., respectively, contact the chamber to cause alternating temperature cycles within the reaction chamber.

The thermocycling devices of the invention further include at least one conduit for conducting the one or more fluids from the fluid sources to contact the reaction chamber. The conduit can include a valve at one end for controlling fluid flow from the fluid source into the conduit. In a certain embodiment, at least one conduit is configured to conduct fluid flow from the one or more fluid sources through the reaction chamber. For example, the thermocycling device of the invention has a main reaction chamber having an inlet and an outlet, and at least one conduit coupled to one or more fluid sources for flowing one or more fluids into the main reaction chamber, the conduit being interconnected with the inlet channel of the main reaction chamber and including a valve at one end for controlling fluid flow into the conduit. Preferably, the thermocycling device is oriented in a position such that fluid flowing into the main reaction chamber flows out through the outlet channel by gravitational force.

Alternatively, the thermocycling devices of the invention can include at least one conduit configured to conduct fluid from one or more fluid sources around the reaction chamber. The reaction chamber can be made of a thermoconductive material to facilitate thermal transfer between the one or more fluids surrounding the reaction chamber and the interior of the chamber.

The thermocycling devices of the invention further include, or are coupled to, a droplet generator for forming droplets containing a nucleic acid template and reagents sufficient for conducting a PCR reaction (e.g., at least one primer, dNTPs and a polyermase and/or reverse transcriptase). The droplet generator can contain a nucleic acid sample introduction unit and a unit for combining the sample with one or more PCR reagents. Alternatively, the droplet generator has an injection orifice which connects a sample flow pathway to a channel containing an immiscible carrier fluid.

The thermocycling devices of the invention can include a heating source for heating the one or more fluid sources to temperatures sufficient for conducting a polymerase chain reaction. The heating source can be embedded/fabricated within the device. Alternatively, the heating source is an external source coupled to the device. In some embodiments, the heating source includes one or more metal coils, wires or films, e.g., tungsten, platinum, or a combination thereof.

The thermocycling devices of the invention can also include a detection module for detecting an analyzing (e.g., quantitating, sequencing) amplicons in the droplet(s).

One or more of the thermocycling devices of the invention can be encased in a housing and arranged in series, such as for example, in a parallel arrangement to each other.

The thermocycling devices of the invention are useful for amplifying nucleic acids, including DNA (PCR) and RNA (reverse transcriptase PCR). One or more droplets are flowed into the main reaction chamber, each droplet comprising reagents sufficient for conducting a polymerase chain and at least one nucleic acid template. Preferably, each droplet includes on average a single nucleic acid template. The polymerase chain reaction is conducted in the main reaction chamber by contacting the chamber with one or more fluids having temperatures sufficient to conduct a PCR reaction, thereby causing alternating temperatures within the reaction chamber.

For example, the reaction chamber is first contacted with a fluid having a temperature sufficient to denature a nucleic acid template (e.g., 94° to 100° Celsius) for a sufficient amount of time to allow denaturing of the nucleic acid template in the droplet(s).

Next, the reaction chamber is contacted with a fluid having an annealing temperature (e.g., 50° to 65° Celsius) for a sufficient amount of time to allow annealing of one or more PCR reagents (e.g., at least one primer) to the nucleic acid template.

Next, the reaction chamber is contacted with a fluid at a temperature sufficient to allow extension of the nucleic acid template by one or more of the PCR reagents (e.g., 68° to 72° Celsius) for a sufficient amount of time. The steps of contacting the reaction chamber with one or more fluids having temperatures sufficient for denaturing, annealing and extension are preferably repeated for one or more cycles, e.g., 20-45 cycles.

Alternating temperatures within the reaction chamber can be achieved by flowing one more fluids having temperatures sufficient to conduct a PCR reaction through the reaction chamber, thereby directly contacting the droplet(s) housed within the chamber, or by flowing the one or more fluids around the reaction chamber, thereby indirectly contacting the droplet(s) housed within the chamber.

Other features and advantages of the invention will be apparent from the following detailed description and claims.

DETAILED DESCRIPTION

Figure 1A:
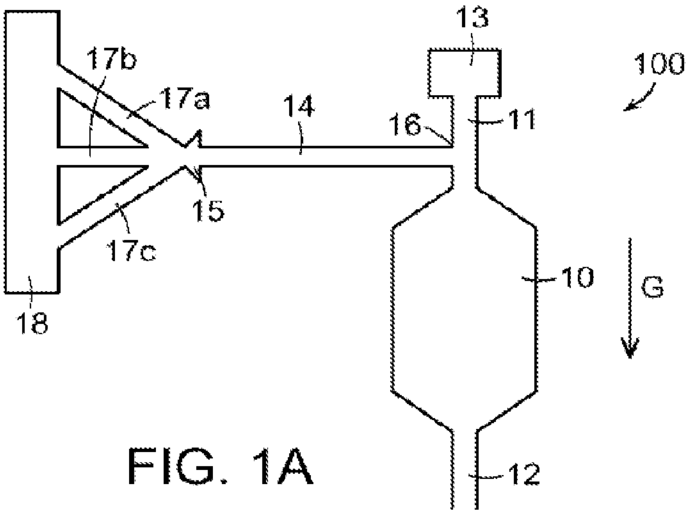
FIGS. 1A-B are schematics illustrating an exemplary embodiment of a thermocycling device according to the invention.

Referring now to the drawings, to the following detailed description, and to incorporated materials; detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Themocycling Devices of the Invention

The invention provides fluid-based thermocycling devices useful for amplification of nucleic acids. The thermocycling devices of the invention utilize at least one reaction chamber and one or more fluid sources having different temperatures sufficient for conducting a PCR reaction that contact the reaction chamber in a manner that causes alternating temperatures within the reaction chamber. In certain embodiments, the thermocycling devices of the invention include more than one reaction chamber. Temperatures for conducting a PCR reaction are well known in the art and typically include a temperature sufficient for denaturing a nucleic acid template (e.g., 94°-100° C.), a temperature sufficient for causing one or more PCR reagents, such as the primers, to anneal to a strand of the denatured nucleic acid template (e.g., 50°-65° C.), and a temperature sufficient to allow extension of each primer in the 5' to 3' direction, duplicating the DNA fragment between the primers (e.g., 68°-72° C.).

The one or more fluid sources can be contained within one or more reservoirs within the thermocycling device. Alternatively, the one or more fluids can be an external fluid source coupled to the device. The devices of the invention include at least one conduit that conducts fluid flow from the one or more fluid sources to contact with the reaction chamber. The conduit can be configured to conduct fluid from the fluid source into the chamber, thereby directly causing alternating temperatures within the reaction chamber. Alternatively, the conduit can be configured to conduct fluid around the reaction chamber, thereby indirectly causing alternating temperatures within the reaction chamber by transfer of thermal energy from the fluid through the walls of the chamber.

Preferably, the thermocycling devices of the invention further include a droplet generator in which droplets comprising picoliter volumes of reagents for conducting a PCR reaction (e.g., forward and reverse primers, dNTPs, and a thermostable enzyme (e.g., polymerase and/or transcriptase)) and nucleic acid template are formed. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc., the contents of each of which are herein incorporated by reference in their entireties. The droplet generator can be integral to the thermocycling device or externally coupled to the device.

In certain embodiments, the thermocycling devices of the invention include a heating source for heating one or more fluids to temperatures sufficient to conduct a PCR reaction. The heating source can be an external heating source (e.g., thermal blocks), or embedded/fabricated within the device. Examples of suitable heating sources include one or more metal wires, coils or films, such as tungsten and/or platinum wires, coils or films. The one or more heating sources are capable of attaining temperatures sufficient to conduct the various stages of a polymerase chain reaction. For example, the one or more heating sources attain a temperature ranging from 94°-100° Celsius for conducting the denaturing stage of a polymerase chain reaction; a temperature ranging from 50°-65° Celsius, for conducting the annealing stage of a polymerase chain reaction; and a temperature ranging from 68°-72° Celsius, for conducting the extension stage of a polymerase chain reaction. Preferably, a separate heating source (i.e., a separate wire, coil or film) is used to attain the different temperature ranges required for each stage.

Figure 1B:
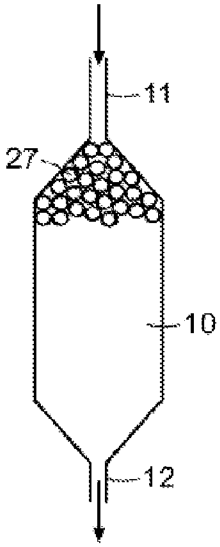

An exemplary embodiment of a fluid based thermocycling device constructed in accordance with the present invention is illustrated in FIGS. 1A-B. In this embodiment, the thermocycling device designated 100 comprises a main reaction chamber 10 having an inlet channel 11 at the top of chamber 10 and an outlet channel 12 at the bottom of chamber 10. The inlet channel 11 is coupled to a droplet generator 13. The thermocycling device 100 further includes a first channel 14 for flowing one or more fluids into the main reaction chamber 10. The first channel 14 has a valve 15 at one end for controlling the flow of one or more fluids into the first channel 14, and is interconnected 16 with inlet channel 11 of the main reaction chamber 10 on the opposite end. One or more second channels, designated 17*a*, 17*b* and 17*c*, are coupled to first channel 14 for flowing one or more fluids through first channel 14 into main reaction chamber 10. Device 100 is oriented such that any fluid which enters main reaction chamber 10 flows through and exits the chamber through outlet channel 12 by gravitational force G. Optionally, outlet channel 12 has a valve for controlling fluid flow out of the main reaction chamber. As shown in FIG. 1, a heating source 18 for heating one or more fluids to temperatures sufficient to conduct a PCR reaction is coupled to second channels 17*a*, 17*b* and 17*c*.

Figure 5:
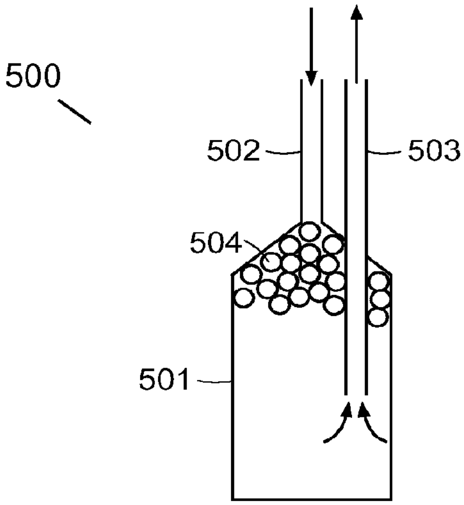
FIG. 5 is a schematic illustrating another exemplary embodiment of a thermocycling device according to the invention.

Another embodiment of a fluid based thermocycling device constructed in accordance with the present invention is illustrated in FIG. 5. In this embodiment, the thermocycling device designated 500 includes a main reaction chamber 501 having a first channel 502 and a second channel 503. Both the first and second channels 502 and 503 are positioned on the same end of chamber 501. The first channel 502 may be coupled to a droplet generator, and also to a fluidic network for flowing one or more fluids into the main reaction chamber 501. The first and second channels 502 and 503 each have a valve at one end for controlling the flow of one or more fluids into the first and second channels 502 and 503. Device 500 is oriented such that any fluid which enters main reaction chamber 501 is maintained in the chamber until it is removed from the chamber through either the first or second channels 502 and 503.

Figure 6A:
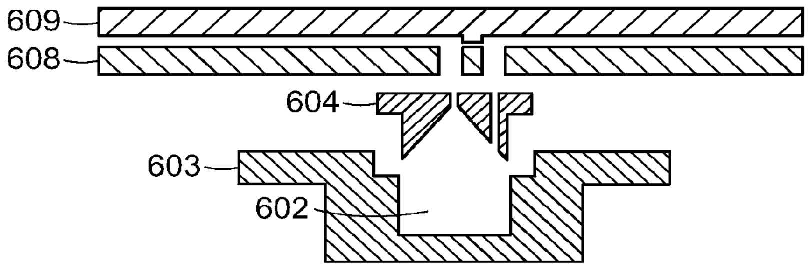
FIGS. 6A-C are schematic illustrating another exemplary embodiment of a thermocycling device according to the invention.
Figure 6B:
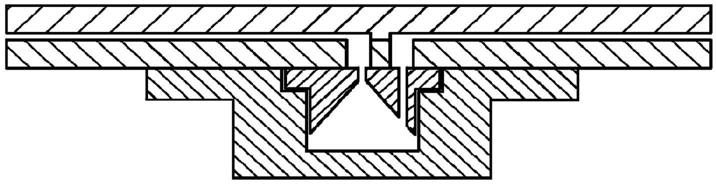
Figure 6C:
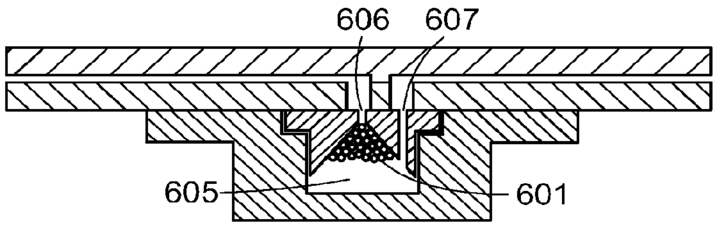
Figures 7A, 7B, 7C, 7D:
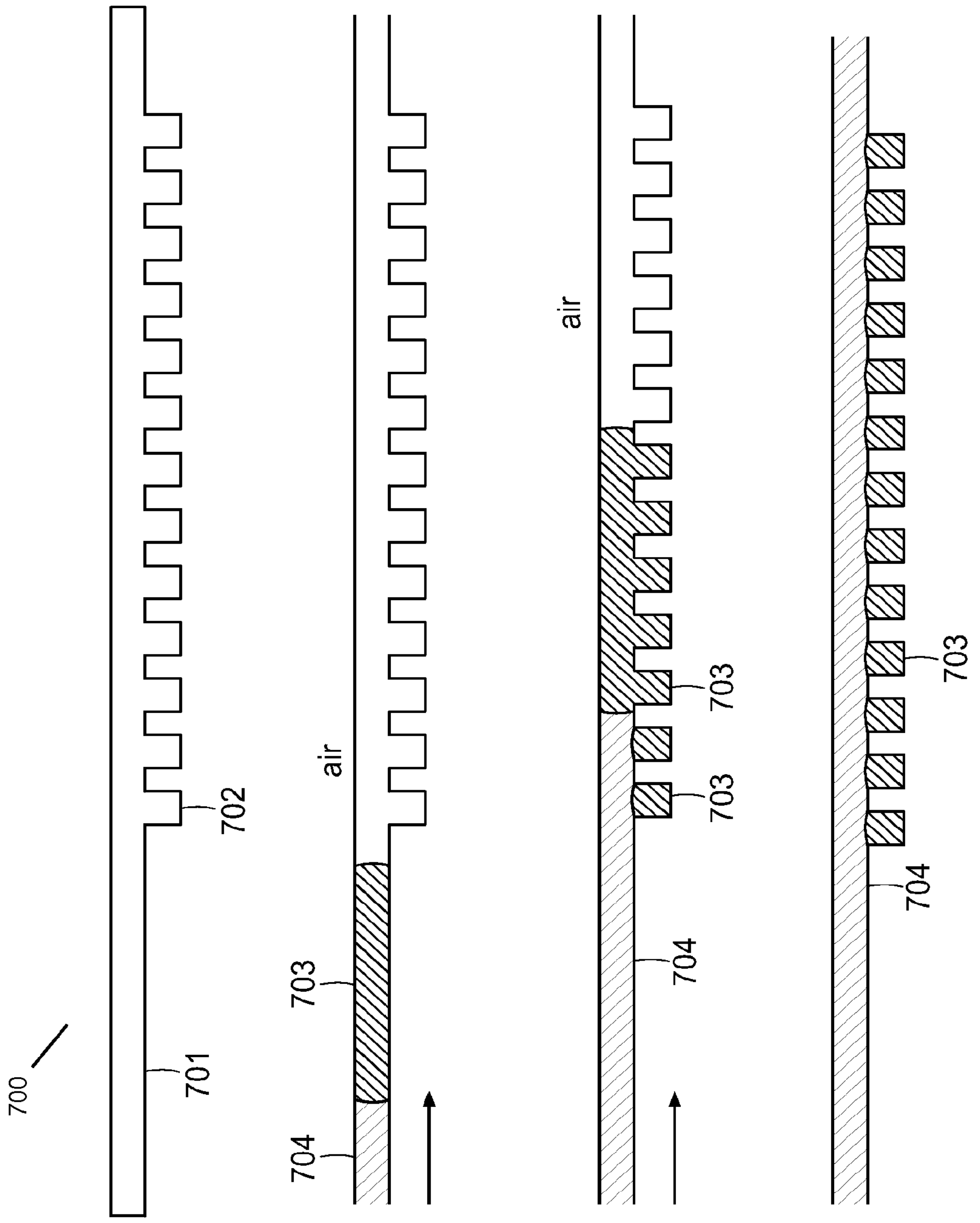
FIGS. 7A-D are schematic illustrating another exemplary embodiment of a thermocycling device according to the invention.
Figure 8A:
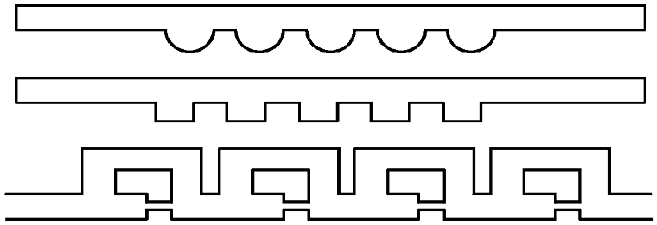
FIGS. 8A-D show exemplary different configurations for the channels and depressions of the device of FIG. 7.
Figure 8B:
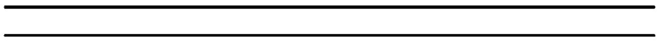
Figure 8C:
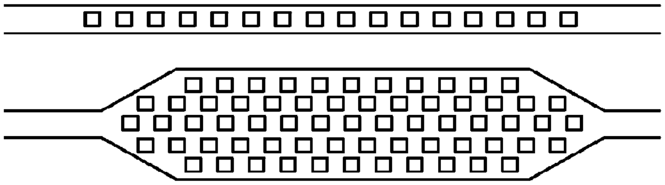
Figure 8D:
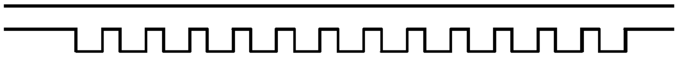

Another exemplary embodiment of a fluid based thermocycling device constructed in accordance with the present invention is illustrated in FIGS. 6A-C. This embodiment illustrates droplet thermocycling devices 600 using a single well plate or a multi-well plate, for example a 96 well plate, a 384 well plate etc. FIG. 6 illustrates using a single well of a plate, however, this description applies to all well of the plate. In this embodiments, droplets 601 are generated off-plate using any droplet generating method known in the art, including the droplet generating methods described herein. The droplets 601 are then dispensed or collected in wells 602 of the well plate 603. An insert 604 that sealably conforms to the size of the well 602 is inserted into the well 602 to form a chamber 605 in the well 602. The insert 604 has a first channel 606 and a second channel 607. After the insert 604 is seated in the well 602, a top plate 608 is placed on top of the insert 602. The top plate has openings that line-up with the first channel 606 and the second channel 607 of the insert 604. A channel plate 609 is then placed on top of the top plate 608. This arrangement forms a fluidic channel for fluid to flow into and out of the chamber 605 created in well 602 by insert 604.

Another exemplary embodiment of a fluid based thermocycling device constructed in accordance with the present invention is illustrated in FIGS. 7A-D. This embodiment illustrates droplet thermocycling device 700 that includes at least one channel 701 that includes depressions 702 in the bottoms of the channel 701. A first fluid 703 is introduced into the channel 701 followed by a second fluid 704 that is immiscible with the first fluid 703. The second fluid 704 pushes the first fluid 703 through the channel 701 such that the first fluid fills the depressions 702 and then becomes enclosed in the depressions 702 since the second fluid 704 creates a barrier, preventing the first fluid 703 from existing the depressions 702. FIGS. 8A-D show exemplary different configurations for the channels and depressions of device 700.

Figure 3:
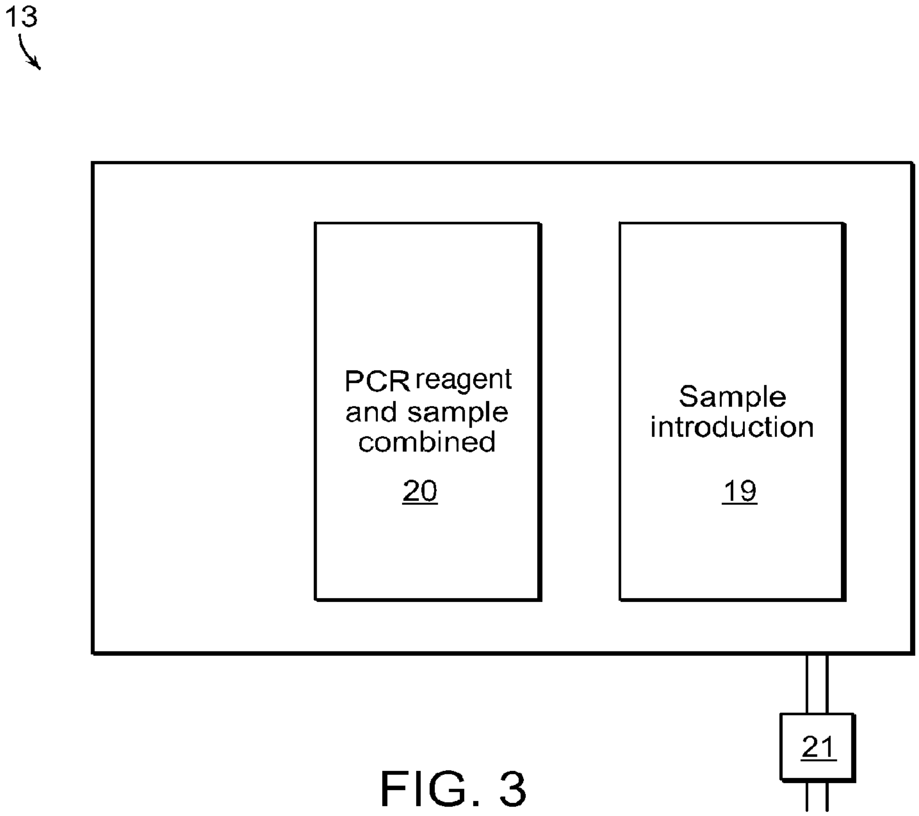
FIG. 3 is an blown-up schematic of an exemplary droplet generator for use in the thermocycling device of the invention.
Figure 4:
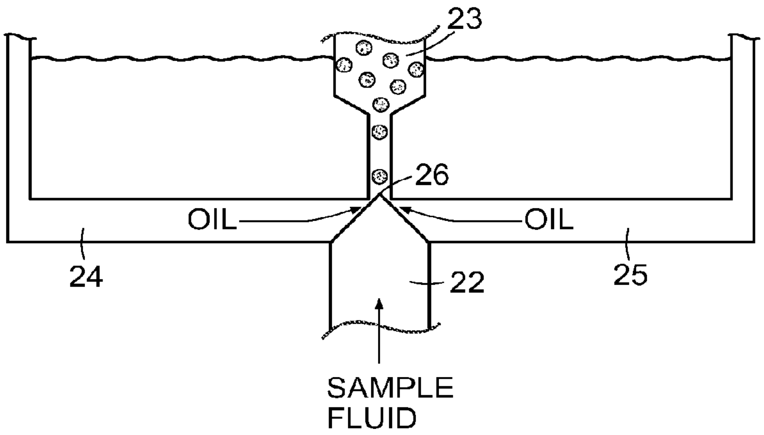
FIG. 4 is a blown-up schematic of another exemplary droplet generator for use in the thermocycling device of the invention.

An exemplary embodiment of a droplet generator that can be used in the device of the invention is shown in FIG. 3. Briefly, the droplet generator 13 comprises a nucleic acid sample introduction unit 19 and a unit 20 where the nucleic acid template and the PCR reagents are combined. The combined template and PCR reagents (i.e., combined sample) are flowed into an injection orifice or microjet 21 which connects the combined sample flow pathway to a channel or tube comprising an immiscible carrier fluid. Injection of the combined sample through orifice 21 captures the combined sample in the immiscible carrier fluid to produce droplets. An alternative exemplary embodiment of a droplet generator 13 that can be used in the device of the invention is shown in FIG. 4. Droplet generator 13 includes an inlet channel 22, and outlet channel 23, and two carrier fluid channels 24 and 25. Channels 22, 23, 24, and 25 meet at a junction 26. Inlet channel 22 flows sample fluid to the junction 26. Carrier fluid channels 24 and 25 flow a carrier fluid that is immiscible with the sample fluid to the junction 105. Inlet channel 101 narrows at its distal portion wherein it connects to junction 26 (See FIG. 4). Inlet channel 22 is oriented to be perpendicular to carrier fluid channels 24 and 25. Droplets are formed as sample fluid flows from inlet channel 22 to junction 26, where the sample fluid interacts with flowing carrier fluid provided to the junction 26 by carrier fluid channels 24 and 25. Outlet channel 23 receives the droplets of sample fluid surrounded by carrier fluid.

The nucleic acid sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid is one that is immiscible with the sample fluid. The carrier fluid can be a non-polar solvent, decane (e g., tetradecane or hexadecane), fluorocarbon oil, silicone oil or another oil (for example, mineral oil). Optionally, the carrier fluid contains one or more additives, such as agents which reduce surface tensions (surfactants). Surfactants can include TWEEN (surfactant, commercially available from Croda International), SPAN (surfactant, commercially available from Sigma Aldrich), fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. In a particular embodiment, the immiscible carrier fluid contains at the fluorosurfactant described in U.S. Published Patent Application No. US20100105112, the contents of which are herein incorporated by reference in its entirety.

Optionally, the thermocycling device of the invention further includes a detection module for detection and analysis of the droplets post-amplification. The detection module can include, for example, a laser (e.g., a blue laser) and a detector for monitoring a colorimetric indicator (e.g., fluorescence or optical absorption) generated with each nucleic acid template duplication sequence.

Figure 2:
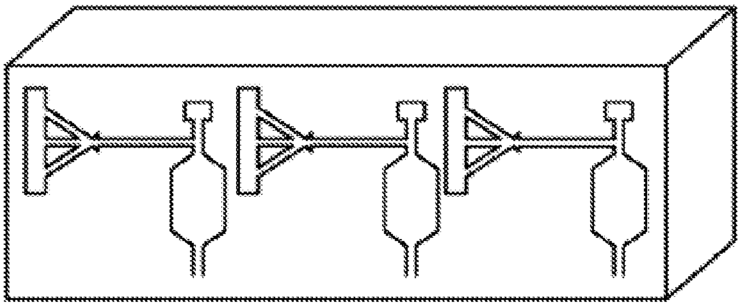
FIG. 2 is a schematic illustrating an apparatus containing a plurality of the thermocycling devices depicted in FIG. 1A.

One or more of the thermocycling devices of the invention can be mounted, embedded or encased in a housing or a substrate. For example, FIG. 2 depicts a plurality of the devices depicted in FIG. 1A encased within a housing. The housing and/or substrate can be a polymer, or a silicon-glass housing, for example.

The thermocycling devices of the invention have significant advantages over typical bulk DNA detection techniques (even microscale bulk solution approaches), including (1) much faster detection time through a reduction in the total number of temperature cycles required, (2) a reduction in the time for each cycle, and (3) removing interference from competing DNA templates. The devices of the invention achieve a reduction in the total number of cycles by limiting the dilution of the optically generated signal (e.g., fluorescence or absorption). The formation of partitioned fluid volumes of the nucleic acid template containing solution effectively isolates the fluid volumes which contain the target nucleic acid template from the fluid volumes that do not contain the target. Therefore, the dilution of the optical signal is largely eliminated, allowing much earlier detection. This effect is directly related to the number of fluid partitions formed from the initial sample/reagent pool.

Isolating the PCR reaction in such small (picoliter) volumes provides an order of magnitude reduction in overall detection time by: (1) reducing the duration of each temperature cycle—the concentration of reactants increases by enclosing them in picoliter type volumes. Since reaction kinetics depend on the concentration of the reactant, the efficiency of a droplet should be higher than in an ordinary vessel (such a test tube) where the reactant quantity is infinitesimal. (2) reducing the total number of cycles—dilution of the fluorescently generated signal is largely eliminated in such a small volume, allowing much earlier detection. This effect is directly related to the number of droplets formed from the initial sample/reagent pool. Since PCR is an exponential process, for example, 1000 droplets would produce a signal 10 cycles faster than typical processing with bulk solutions. (3) removing interference from competing DNA templates—given the extremely small volumes involved, it is possible to isolate a single template of the target DNA in a given droplet. A picoliter (pL) microdoplet filled with a 1 pM solution, for example, will be occupied by only one molecule on average. This makes it possible to amplify only one template in mixtures containing many kinds of templates without interference.

Nucleic Acid Amplification

The present invention also provides methods of nucleic acid amplification using the thermocycling devices of the invention. In certain embodiments, the amplification reaction is a polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

Methods for performing PCR in droplets are shown for example in Link et al. (U.S. patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc., the content of each of which is incorporated by reference herein in its entirety.

Briefly, droplets of picoliter volumes are formed by the droplet generator, as previously described, each droplet containing on average a single nucleic acid template and PCR reagents sufficient for conducting a polymerase chain reaction (e.g., primers, dNTPs, and a thermostable enzyme (e.g., polymerase and/or reverse transcriptase)).

One or more droplets containing the nucleic acid template and PCR reagents are flowed into the reaction chamber. One or more fluids having temperatures sufficient for conducting a PCR reaction are contacted with the reaction chamber to cause alternating temperatures within the interior of the chamber. The one or more fluids are contacted with the chamber for sufficient amounts of time to conduct the different stages (i.e., denaturing, annealing, extension) of a PCR reaction.

The one or more fluids can flow directly into the chamber, thereby directly bathing the droplets. Alternatively, the one or more fluids can flow around the chamber, thereby indirectly contacting the droplets by thermal transfer.

With reference to the exemplary embodiment of the thermocycling device illustrated in FIGS. 1A-B, one or more droplets 27 are flowed through inlet channel 11 into the main reaction chamber 10. A first fluid having a temperature sufficient for denaturing the nucleic acid template (e.g., 94°-100° Celsius) is flowed from a second channel (e.g., 17*a*), through first channel 14, and into the main reaction chamber 10 via inlet 11. The first fluid is maintained in reaction chamber 10 for a sufficient time to allow denaturing of the nucleic acid template (e.g., 2-5 minutes), then exits the main reaction chamber through outlet 12 by gravitational force.

A second fluid having a temperature sufficient for allowing one or more of the PCR reagents (e.g., primers) to anneal/hybridize to the denatured template (e.g., 50°-65° Celsius) is flowed from a second channel (e.g., 17*b*), through first channel 14, and into the main reaction chamber 10 via inlet 11. The second fluid is maintained in reaction chamber 10 for a sufficient time to allow annealing (e.g., 20-45 seconds), then exits the main reaction chamber through outlet 12 by gravitational force.

A third fluid having a temperature sufficient for allowing extension of the nucleic acid template (e.g., 68°-72° Celsius) is flowed from a second channel (e.g., 17*c*), through first channel 14, and into the main reaction chamber 10 via inlet 11. The third fluid is maintained in reaction chamber 10 for a sufficient time to allow extension of the nucleic acid template (~1 min/kb), then exits the main reaction chamber through outlet 12 by gravitational force. These cycles of denaturing, annealing and extension can be repeated for 20-45 additional cycles, resulting in amplification of the nucleic acid template in each droplet.

With reference to the exemplary embodiment of the thermocycling device illustrated in FIG. 5, the system is purged by flowing a fluid that is immiscible with an aqueous droplet, such as oil, through first channel 502 and out second channel 503. This is performed until chamber 501 is filled with the immiscible fluid and free of air. The, one or more droplets 504 are flowed through first channel 502 into the main reaction chamber 501. The immiscible fluid is displaced through second channel 503 as the droplets 504 enter the chamber 501. A first fluid having a temperature sufficient for denaturing the nucleic acid template (e.g., 94°-100° Celsius) is flowed from the fluidic network and into the main reaction chamber 501 via channel 502. The first fluid is maintained in reaction chamber 501 for a sufficient time to allow denaturing of the nucleic acid template (e.g., 2-5 minutes), then exits the main reaction chamber 501 through channel 503.

A second fluid having a temperature sufficient for allowing one or more of the PCR reagents (e.g., primers) to anneal/hybridize to the denatured template (e.g., 50°-65° Celsius) is flowed from the fluidic network and into the main reaction chamber 501 via channel 502. The second fluid is maintained in reaction chamber 501 for a sufficient time to allow annealing (e.g., 20-45 seconds), then exits the main reaction chamber 501 through channel 503.

A third fluid having a temperature sufficient for allowing extension of the nucleic acid template (e.g., 68°-72° Celsius) is flowed from the fluidic network and into the main reaction chamber 501 via channel 502. The third fluid is maintained in reaction chamber 501 for a sufficient time to allow extension of the nucleic acid template (~1 min/kb), then exits the main reaction chamber through channel 503. These cycles of denaturing, annealing and extension can be repeated for 20-45 additional cycles, resulting in amplification of the nucleic acid template in each droplet. Once completed, flow in device 500 is reversed so that droplets 504 may exit through channel 502.

With reference to the exemplary embodiment of the thermocycling device illustrated in FIGS. 6A-C, the system is purged by flowing a fluid that is immiscible with an aqueous droplet, such as oil, through the channel produced in the plate such that the immiscible fluid flows through the first channel 606 and out second channel 607. This is performed until chamber 605 is filled with the immiscible fluid and free of air. The, one or more droplets 601 are flowed through the channel produced in the plate such that they flow through the first channel 606 into the main reaction chamber 605. The immiscible fluid is displaced through second channel 607 as the droplets 601 enter the chamber 605. A first fluid having a temperature sufficient for denaturing the nucleic acid template (e.g., 94°-100° Celsius) is flowed from the fluidic network and into the main reaction chamber 605 via the channel in the plate and through channel 606 and into the chamber 605. The first fluid is maintained in reaction chamber 605 for a sufficient time to allow denaturing of the nucleic acid template (e.g., 2-5 minutes), then exits the main reaction chamber 605 through channel 607.

A second fluid having a temperature sufficient for allowing one or more of the PCR reagents (e.g., primers) to anneal/hybridize to the denatured template (e.g., 50°-65° Celsius) is flowed from the fluidic network and into the main reaction chamber 605 via channel 606. The second fluid is maintained in reaction chamber 605 for a sufficient time to allow annealing (e.g., 20-45 seconds), then exits the main reaction chamber 605 through channel 607.

A third fluid having a temperature sufficient for allowing extension of the nucleic acid template (e.g., 68°-72° Celsius) is flowed from the fluidic network and into the main reaction chamber 605 via channel 606. The third fluid is maintained in reaction chamber 605 for a sufficient time to allow extension of the nucleic acid template (~1 min/kb), then exits the main reaction chamber through channel 607. These cycles of denaturing, annealing and extension can be repeated for 20-45 additional cycles, resulting in amplification of the nucleic acid template in each droplet. Once completed, flow in device 600 is reversed so that droplets 601 may exit through channel 606.

With reference to the exemplary embodiment of the thermocycling device illustrated in FIGS. 7A-D, the temperature of the immiscible fluid 704 is cycled, thereby cycling the temperature of the fluid 703 containing the nucleic acids. Fluid 704 is heated to a temperature sufficient for denaturing the nucleic acid template (e.g., 94°-100° Celsius) and maintained at that temperature for a sufficient time to allow denaturing of the nucleic acid template (e.g., 2-5 minutes). Fluid 704 is then cooled to a temperature sufficient for allowing one or more of the PCR reagents (e.g., primers) to anneal/hybridize to the denatured template (e.g., 50°-65° Celsius) and maintained at that temperature for a sufficient time to allow sufficient time to allow annealing (e.g., 20-45 seconds). Fluid 704 is then heated to a temperature sufficient for allowing extension of the nucleic acid template (e.g., 68°-72° Celsius) and maintained at that temperature for a sufficient time to allow extension of the nucleic acid template (~1 min/kb). These cycles of denaturing, annealing and extension can be repeated for 20-45 additional cycles, resulting in amplification of the nucleic acid template in each portion of fluid 703 in each depression 702.

Target Detection

As previously described, device 100 can include a detection module. After amplification, droplets are flowed to a detection module for detection of amplification products. The droplets may be individually analyzed and detected using any methods known in the art, such as detecting for the presence or amount of a reporter. Generally, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In certain embodiments, amplified target are detected using detectably labeled probes. In particular embodiments, the detectably labeled probes are optically labeled probes, such as fluorescently labeled probes. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY (boron-dipyrromethene fluorescent dye, Life Technologies, Inc.); Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'- disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (CIBACRON Brilliant Red 3B-A (monochlorotriazine dye, Santa Cruz Biotech)) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (TEXAS RED; sulforhodamine 101 acid chloride, Life Technologies, Inc.); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; CY3 (cyanine 3 fluorescent dye, Amersham); CY5 (cyanine 5 fluorescent dye, Amersham); CY5.5 (cyanine 5.5 fluorescent dye, Amersham); CY7 (cyanine 7 fluorescent dye, Amersham); IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

During amplification, fluorescent signal is generated in a TAQMAN (Taq polymerase, commercially available from Life Technologies) assay by the enzymatic degradation of the fluorescently labeled probe. The probe contains a dye and quencher that are maintained in close proximity to one another by being attached to the same probe. When in close proximity, the dye is quenched by fluorescence resonance energy transfer to the quencher. Certain probes are designed that hybridize to the wide-type of the target, and other probes are designed that hybridize to a variant of the wild-type of the target. Probes that hybridize to the wild-type of the target have a different fluorophore attached than probes that hybridize to a variant of the wild-type of the target. The probes that hybridize to a variant of the wild-type of the target are designed to specifically hybridize to a region in a PCR product that contains or is suspected to contain a single nucleotide polymorphism or small insertion or deletion.

During the PCR amplification, the amplicon is denatured allowing the probe and PCR primers to hybridize. The PCR primer is extended by Taq polymerase replicating the alternative strand. During the replication process the Taq polymerase encounters the probe which is also hybridized to the same strand and degrades it. This releases the dye and quencher from the probe which are then allowed to move away from each other. This eliminates the FRET between the two, allowing the dye to release its fluorescence. Through each cycle of cycling more fluorescence is released. The amount of fluorescence released depends on the efficiency of the PCR reaction and also the kinetics of the probe hybridization. If there is a single mismatch between the probe and the target sequence the probe will not hybridize as efficiently and thus a fewer number of probes are degraded during each round of PCR and thus less fluorescent signal is generated. This difference in fluorescence per droplet can be detected and counted. The efficiency of hybridization can be affected by such things as probe concentration, probe ratios between competing probes, and the number of mismatches present in the probe.

EQUIVALENTS

The device and methods of invention are susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

What is claimed is:

1. A thermocycling device for amplifying nucleic acid in a droplet, the device comprising:
- a reaction chamber comprising a plurality of droplets;
- a first temperature-controlled fluid source comprising a fluid at a first temperature;
- a second temperature-controlled fluid source comprising a fluid at a second temperature; and
- a conduit fluidly coupled to the first and the second temperature-controlled fluid sources, and the reaction chamber;
  - wherein the device is adapted to immerse the plurality of droplets in the fluid at the first temperature within the reaction chamber and subsequently immerse the plurality of droplets in the fluid at the second temperature within the reaction chamber, wherein the reaction chamber is oriented so that a gravitational force causes the fluid at the first temperature and the fluid at the second temperature to exit the reaction chamber while maintaining the plurality of droplets in the reaction chamber.

2. The device of claim 1, further comprising a third temperature-controlled fluid source at a third temperature, and the fluid at the first temperature is about 94°-100° Celsius, the fluid at the second temperature is about 50°-65° Celsius, and the fluid at the third temperature is about 68°-72° Celsius.

3. The device of claim 1, wherein the conduit conducts the fluid of the first and second temperatures from said temperature-controlled fluid sources through the reaction chamber.

4. The device of claim 1, wherein said reaction chamber comprises an inlet and an outlet, and said fluid at a first temperature and said fluid at a second temperature flows into said inlet and out of said outlet.

5. The device of claim 4, wherein the conduit is fluidly coupled to the inlet and comprises a valve at one end for controlling flow from the first or second temperature-controlled fluid into the conduit.

6. The device of claim 1, further comprising a droplet generator.

7. The device of claim 6, wherein the droplet generator comprises a nucleic acid sample introduction unit and a unit for combining the sample with one or more PCR reagents.

8. The device of claim 6, wherein the droplet generator comprises an injection orifice which connects a sample flow pathway to a channel comprising an immiscible carrier fluid.

9. The device of claim 6, wherein the droplet generator comprises an inlet channel for flowing a sample fluid, an outlet channel, and two carrier fluid channels for flowing an immiscible carrier fluid, each of the channels intersecting at a junction, said inlet and outlet channels being perpendicular to the carrier fluid channels, and said inlet channel being narrower at a distal portion where it connects to the junction.

10. The device of claim 1, further comprising a heating source in proximity to the first or second temperature-controlled fluid source.

11. The device of claim 10, wherein the heating source is embedded within the device.

12. The device of claim 11, wherein the heating source is a metal selected from the group consisting of tungsten and platinum.

13. The device of claim 10, wherein the heating source is an external heating source.

14. The device of claim 10, wherein the heating source is selected from the group consisting of a coil, a wire and a film.

15. The device of claim 1, further comprising a detection module.

16. An apparatus for nucleic acid amplification comprising a plurality of the device of claim 1.

17. A method of nucleic acid amplification, said method comprising the steps of:

a) providing a reaction chamber for housing a plurality of droplets;

b) flowing the plurality of droplets into the reaction chamber, each droplet comprising a single nucleic acid template, at least one primer and reagents sufficient for nucleic acid amplification;

c) flowing a first fluid having a first temperature into the reaction chamber and maintaining for a sufficient time to denature the nucleic acid template in the droplets, wherein the reaction chamber is oriented so that a gravitational force causes the first fluid to exit the reaction chamber while maintaining the droplets in the reaction chamber;

d) flowing a second fluid having a second temperature into the reaction chamber and maintaining for a sufficient time to anneal one or more of the PCR reagents to the nucleic acid template in the droplets, wherein the reaction chamber is oriented so that a gravitational force causes the second fluid to exit the reaction chamber while maintaining the droplets in the reaction chamber;

e) flowing a third fluid having a third temperature into the reaction chamber and maintaining for a sufficient time to extend the nucleic acid template in the droplets, wherein the reaction chamber is oriented so that a gravitational force causes the third fluid to exit the reaction chamber while maintaining the droplets in the reaction chamber.

18. The method of claim 17, wherein said first fluid has a temperature range from 94°-10020 Celsius, said second fluid has a temperature range from 50°-65° Celsius and said third fluid has a temperature range from 68°-72° Celsius.

19. The method of claim 17, wherein steps c) through e) are repeated for one or more cycles.

20. The method of claim 19, wherein steps c) through e) are repeated for 20-45 cycles.

21. The method of claim 17, wherein said first, second and third fluids directly contact the one or more droplets.

* * * * *